(12) United States Patent
Cole

(10) Patent No.: US 10,369,118 B2
(45) Date of Patent: Aug. 6, 2019

(54) METHOD OF REDUCING SCARRING

(71) Applicant: Cole Research & Design, Inc., Jackson, MS (US)

(72) Inventor: Jeptha N. Cole, Jackson, MS (US)

(73) Assignee: Cole Research & Design, LLC, Jackson, MS (US)

( * ) Notice: Subject to any disclaimer, the term of this patent is extended or adjusted under 35 U.S.C. 154(b) by 0 days.

(21) Appl. No.: 15/492,766

(22) Filed: Apr. 20, 2017

(65) Prior Publication Data

US 2017/0281563 A1     Oct. 5, 2017

Related U.S. Application Data

(63) Continuation of application No. 14/313,338, filed on Jun. 24, 2014, now abandoned.

(60) Provisional application No. 61/839,769, filed on Jun. 26, 2013.

(51) Int. Cl.

| *A61K 31/05* | (2006.01) |
|---|---|
| *A61P 17/02* | (2006.01) |
| *A61K 45/06* | (2006.01) |
| *A61L 26/00* | (2006.01) |
| *A61K 31/203* | (2006.01) |
| *A61K 31/352* | (2006.01) |
| *A61K 31/728* | (2006.01) |

(52) U.S. Cl.
CPC ............ *A61K 31/05* (2013.01); *A61K 31/203* (2013.01); *A61K 31/352* (2013.01); *A61K 31/728* (2013.01); *A61K 45/06* (2013.01); *A61L 26/0019* (2013.01); *A61L 26/0023* (2013.01); *A61L 26/0066* (2013.01); *A61P 17/02* (2018.01); *A61L 2430/34* (2013.01)

(58) Field of Classification Search
CPC ................................ A61K 31/05; A61P 17/02
See application file for complete search history.

(56) References Cited

U.S. PATENT DOCUMENTS

| 7,026,518 B2 | 4/2006 | Gokaraju |
| 2001/0041684 A1 | 11/2001 | Lezdey et al. |
| 2008/0057088 A1 | 3/2008 | Blass et al. |
| 2008/0139507 A1 | 6/2008 | Gupta |
| 2009/0220450 A1 | 9/2009 | Green et al. |
| 2011/0038965 A1 | 2/2011 | McKay et al. |
| 2011/0245345 A1 | 10/2011 | Amato et al. |
| 2013/0108700 A1* | 5/2013 | Nguyen ............... A61K 38/014 424/488 |
| 2013/0267547 A1 | 10/2013 | Gerk |
| 2014/0275266 A1 | 9/2014 | Wang et al. |
| 2015/0005391 A1 | 1/2015 | Cole |
| 2017/0183290 A1 | 6/2017 | Elsohly et al. |

FOREIGN PATENT DOCUMENTS

| CN | 1915988 | 2/2007 | |
| CN | 101507733 | 8/2009 | |
| CN | 102675100 | 9/2012 | |
| CN | 103508981 | 1/2014 | |
| DE | 20 2011 108805 | 9/2012 | |
| EP | 2 522 330 | 11/2012 | |
| WO | 2004/000302 | 12/2003 | |
| WO | WO-2007143631 A2 * | 12/2007 | ............ A61K 31/05 |
| WO | 2012/048204 | 4/2012 | |
| WO | 2012/129499 | 9/2012 | |
| WO | 2013/068758 | 5/2013 | |
| WO | 2014/126370 | 8/2014 | |
| WO | 2014/210308 | 12/2014 | |
| WO | 2016/057831 | 4/2016 | |
| WO | 2017/019709 | 2/2017 | |

OTHER PUBLICATIONS

Khanna et al., "Dermal Wound Healing Properties of Redox-Active Grape Seed Proanthocyanidins," Free Radical Biology & Medicine, vol. 33, No. 8, pp. 1089-1096, 2002. (Year: 2002).*
Hung et al., "Delivery of Resveratrol, a Red Wine Polyphenol, from Solutions and Hydrogels via the Skin," Biol. Pharm. Bull. 31(5) 955-962 (2008). (Year: 2008).*
Zhu et al., "Effect of Resveratrol on Human Scar Fibroblasts and Scar-Derived Fibroblasts of Rabbit Ears," Chinese Journal of Natural Medicine 2006, vol. 8, No. 1, pp. 7-9. (Year: 2006).*
Translation of Zhu et al. (Chinese Journal of Natural Medicine 2006, vol. 8, No. 1, pp. 7-9), prepared Nov. 2016. (Year: 2016).*
5 Pages, Jan. 25, 2018, 14742647.2, EP.
21 Pages, May 23, 2018, U.S. Appl. No. 15/389,674, US.
International Search Report dated Nov. 7, 2017 for PCT Application No. PCT/US2017/020980.
Ehrlich, H. et al., "Regulation of wound healing from a connective tissue perspective", Wound Repair and Regeneration, vol. 4, issue 2, pp. 203-210, (1996).
Leung, A. et al., "Fetal wound healing: implictions for minimal scar formation", Current Opinion in Pediatrics, vol. 24, No. 3, pp. 371-378, (2012).
Manuel, J. et al., "Matrix metalloproteinase 9 (MMP-9) is upregulated during scarless wound healing in athymic nude mice", Matrix Biology, vol. 25, pp. 505-514, (2006).
Seifert, A.W. et al., "Skin regeneration in adult axolotls: a blueprint for scar-free healing in vertebrates", PLoS One, vol. 7, issue 4, pp. 1-19, (2012).
Polette, M. et al., "Tumor invasion and matrix metalloproteinases", Critical Reviews in Oncology Hematology, vol. 49, pp. 179-186, (2004).
Salo, T. et al., "Expression of matrix metalloproteinase-2 and -9 during early human wound healing", Laboratory Investigation, vol. 70, No. 2, pp. 176-182, (1994).
Giannelis, G., "Matrix metalloproteinases in starless wound healing", Electronic Theses and Dissertations, pp. 1-119, (2011), available at hdl.handle.net/2429/36241.

(Continued)

*Primary Examiner* — Theodore R. West
(74) *Attorney, Agent, or Firm* — Evan Law Group LLC

(57) ABSTRACT

A method for reducing scarring comprises applying into a wound a composition comprising resveratrol. The wound was formed at most one day before the applying, and no part of the skin surface of the wound is more than 3 cm from uninjured skin.

11 Claims, No Drawings

(56) References Cited

OTHER PUBLICATIONS

Guo, M-S. et al., "Hyaluronic acid increases MMP-2 and MMP-9 expressions in cultured trabecular meshwork cells from patients with primary open-angle glaucoma", Molecular Vision, vol. 18, pp. 1175-1181, (2012).
Ndiaye, M. et al., "The grape antioxidant resveratrol for skin disorders: promise, prospects, and challenges", Arch Biochem Biophys., vol. 508, No. 2, pp. 164-170, (2011).
Gweon, E.J. et al., "Resveratrol induces MMP-9 and cell migration via the p38 kinase and PI-3K pathways in HT1080 human fibrosarcoma cells", Oncology Reports, vol. 29, No. 2, pp. 826-834, (2013).
Ghosh, S. et al., "Resveratrol activates SIRT1 in a Lamin A-dependent manner", Cell Cycle, vol. 12, No. 6, pp. 872-876, (2013).
Blander, G. et al., "SIRT1 promotes differentiation of normal human keratinocytes", Journal of Investigative Dermatology, vol. 129, No. 1, pp. 41-49, (2009).
Thompson, N.L. et al., "Expressions of transforming growth factor-β1 in specific cells and tissues of adult and neonatal mice", The Journal of Cell Biology, vol. 108, pp. 661.669, (1989).
Midgley, A. et al., "Transforming growth factor-β1 (TGF-(β1)-stimulated fibroblast to myofibroblast differentiation is mediated by hyaluronan (HA)-facilitated epidermal growth factor receptor (EGFR) and CD44 co-localization in lipid rafts", Journal of Biological Chemistry, vol. 288, No. 21, pp. 14824-14838, (2013).
Busch, F. et al., "Sirt-1 is required for the inhibition of apoptosis and inflammatory responses in human tenocytes", Journal of Biological Chemistry, vol. 287, No. 31, pp. 25770-25781, (2012).
Spallotta, F. et al., "A nitric oxide-dependent cross-talk between class I and III histone deacetylases accelerates skin repair", Journal of Biological Chemistry, vol. 288, No. 16, pp. 11004-11012, (2013).
Pastore, S. et al., "Resveratrol induces long-lasting IL-8 expression and peculiar EGFR activation/distribution in human keratinocytes: Mechanisms and implications for skin administration", PLOS One, vol. 8, issue 3, pp. 1-14, (2013).
Jiang, W.G. et al., "Influence of interleukin-8 (IL-8) and IL-8 receptors on the migration of human keratinocytes, the role of PLC-gamma and potential clinical implications", Experimental and Therapeutic Medicine, vol. 3, No. 2, pp. 231-236, (2012).
Steiger, S. et al., "Neutrophil cannibalism triggers transforming growth factor β1 production and self regulation of neutrophil inflammatory function in monosodium urate monohydrate crystal-induced inflammation in mice", Arthritis & Rheumatism, vol. 65, No. 3, pp. 815-823, (2013).
Holian, O. et al., "Resveratrol inhibits the proliferation of normal human keratinocytes in vitro", Journal of Cellular Biochemistry Supplement, supplement 36, pp. 55-62, (2001).
Kim, J-J. et al., "The role of SIRT1 on angiogenic and odontogenic potential in human dental pulp cells", Journal of endodontics, vol. 38, No. 7, pp. 899-906, (2012).
Williams, L.D. et al., "Safety studies conducted on high-purity trans-resveratrol in experimental animals", Food and Chemical Toxicology, vol. 47, No. 9, pp. 2170-2182, (2009).
Polonini, H.C. et al., "Photoprotective activity of resveratrol analogues", Bioorganic & Medicinal Chemistry, vol. 21, No. 4, pp. 964-968, (2013).
Hung, C-F. et al., "Delivery of resveratrol, a red wine polyphenol, from solutions and hydrogels via the skin", Biological & Pharmaceutical Bulletin, vol. 31, No. 5, pp. 955-962, (2008).
Alonso, C. et al., "Antioxidant cosmeto-textiles: skin assessment", European Journal of Pharmaceutics and Biopharmaceutics, vol. 84, No. 1, pp. 192-199, (2013).
Fagone, E. et al., "Resveratrol inhibits transforming growth factor-β-induced proliferation and differentiation of ex vivo human lung fibroblasts into myofibroblasts through ERK/Akt inhibition and PTEN restoration", Experimental Lung Research, vol. 37, No. 3, pp. 162-174, (2011).

Sheu, S-Y. et al., "Biological characterization of oxidized hyaluronic acid/resveratrol hydrogel for cartilage tissue engineering", Journal of Biomedical Materials Research Part A, vol. 101, issue 12, pp. 3457-3466, (2013).
Fearmonti, R. et al., "A review of scar scales and scar measuring devices", Eplasty, vol. 10, pp. 354-363, (2010).
Nayor, D. et al., "Living longer, healthier lives with resveratrol", Le Magazine, 12 pages, found at www.lef.org, (2008).
Definition of "Resveratrol", Wikipedia, the free encyclopedia, found at www.en.wikipedia.org/wiki/Resveratrol, pp. 1-14, printed on Jun. 21, 2013.
New-Skin® Liquid Bandage, Cover. Protect. Prevent., www.newskinproducts.com/liquid-bandages/liquid-bandage/, pp. 1-10, printed on Apr. 26, 2015.
Edward, M. et al., "Keratinocytes stimulate fibroblast hyaluronan synthesis through the release of stratifin: A possible role in the suppression of scar tissue formation", Wound Repair and Regeneration, vol. 19, pp. 379-386, (2011).
International Search Report dated Oct. 9, 2014 for PCT Application No. PCT/US2014/044338, 13 pages.
Lorena, D. et al., "Normal scarring: importance of myofibroblasts", VVound Repair and Regeneration, vol. 10, No. 2, pp. 86-92, (2002).
Yaman, I. et al., "Effects of resveratrol on incisional wound healing in rats", Surgery Today, vol. 43, No. 12, pp. 1433-1438, (2013).
Fehrholz, M. et al., "Caffeine and rolipram affect smad signaling and TGF-β1 stimulated CTGF and transgelin expression in lung epithelial cells", PLOS One, vol. 9, issue 5, pp. 1-11, 2014.
Gressner, O.A. et al., "Identification of paraxanthine as the most potent caffeine-derived inhibitor of connective tissue growth factor expression in liver parenchymal cells", Liver International, vol. 29, No. 6, pp. 886-897, (2009).
Herman, A. et al., "Caffeine's mechanisms of action and its cosmetic use", Skin Pharmacology and Physiology, vol. 26, No. 1, pp. 8-14, (2013).
Inder, M.K. et al., "Bovine popular stomatitis virus encodes a functionally distinct BEGF that binds both VEGFR-1 and VEGFR-2", Journal of General Virology, vol. 88, pp. 781-791, 2007.
Lee, S. et al., "Effect of a broad-specificity chemokine-binding protein on brain leukocyte infiltration and infarct development", Stroke, vol. 46, pp. 537-544, (2015).
Ojeh, N. et al., "The effects of caffeine on wound healing", International Wound Journal, pp. 1-9, (2014).
Jagtap, S. et al., "All-trans retinoic acid and basic fibroblast growth factor synergistically direct pluripotent human embryonic stem cells to extraembryonic lineages", Stem Cell Research, vol. 10, pp. 228-240, (2013).
Cao, K. et al., "Progerin and telomere dysfunction collaborate to trigger cellular senescence in normal human fibroblasts", The Journal of Clinical Investigation, vol. 121, No. 7, pp. 2833-2844, (2011).
Machesney, M. et al., "Activated keratinocytes in the epidermis of hypertrophic scars", American Journal of Pathology, vol. 152, No. 5, pp. 1133-1141, (1998).
Demidenko, Z.N. et al., "At concentrations that inhibit mTOR, resveratrol suppresses cellular senescence", Cell Cycle, vol. 8, No. 12, pp. 1901-1904, (2009).
Bennett, R.D. et al., "Calmodulin-like protein upregulates myosin-10 in human keratinocytes and is regulated during epidermal wound healing in vivo", Journal of Investigative Dermatology, vol. 129, pp. 765-769, (2009).
Lansdown, A.B.G. et al., "Zinc in wound healing: Theoretical, experimental, and clinical aspects", Wound Repair and Regeneration, vol. 15, pp. 2-16, (2007).
Bennett, R.D. et al., "Calmodulin-like protein increases filopodia-dependent cell motility via up-regulation of myosin-10*", The Journal of Biological Chemistry, vol. 282, No. 5, pp. 3205-3212, (2007).
Skelding, K.A. et al., "Controlling the cell cycle: The role of calcium/calmodulin-stimulated protein kinases I and II", Cell Cycle, vol. 10, issue 4, pp. 631-639, (2011).
Chifflet, S. et al., "Early and late calcium waves during wound healing in corneal endothelial cells", Wound Repair and Regeneration, vol. 20, pp. 28-37, (2012).

(56) References Cited

OTHER PUBLICATIONS

Lansdown, A.B.G., "Calcium: a potential central regulator in wound healing in the skin", Wound Repair and Regeneration, vol. 10, No. 5, pp. 271-285, (2002).

Grzesiak, J.J. et al., "Changes in the concentrations of extracellular $Mg^{++}$ and $Ca^{++}$ down-regulate e-cadherin and up-regulate $\alpha_2 \beta_1$ integrin function, activating keratinocyte migration on type I collagen", Journal of Investigative Dermatology, vol. 104, pp. 768-774, (1995).

Ferreira, A.M. et al., "Diminished induction of skin fibrosis in mice with MCP-1 deficiency" Journal of Investigative Dermatology, vol. 126, pp. 1900-1908, (2006).

Ishimoto, T. et al., "Downregulation of monocyte chemoattractant protein-1 involving short interfering RNA attenuates hapten-induced contact hypersenistivity", Molecular Therapy, vol. 16, No. 2, pp. 387-395, (2008).

De Filippo, K. et al., "Mast cell and macrophage chemokines CXCL1/CXCL2 control the early stage of neutrophil recruitment during tissue inflammation", Blood, vol. 121, No. 24, pp. 4930-4937, (2013).

Qu, L. et al., "Disruption of TLR3 signaling due to cleavage of TRIF by the Hepatitis A virus protease-polymerase processing intermediate, 3CD", PLoS Pathogens, vol. 7, issue 9, pp. 1-13, (2011).

Xiang, Z. et al., "Enterovirus 68 3C protease cleaves TRIF to attenuate antiviral responses mediated by toll-like receptor 3", Journal of Virology, vol. 68, No. 12, pp. 6650-6659, (2014).

Farina, G. et al., "sdRNA activation of endothelin-1 and markers of vascular activation in endothelial cells and fibroblasts", Ann Rheum Dis, vol. 70, pp. 544-550, (2011).

Kim, M.Y. et al., "Hyaluronic acid oligosaccharides suppress TLR3-dependent cytokine expression in a TLR4-dependent manner", PLoS One, vol. 8, issue 8, pp. 1-7, (2013).

Product description of "CCL2 (ID 6347) Trilencer-27 Human siRNA", amsbio, AMS Biotechnology, 1 page, found at www.amsbio.com/datasheets/SR304273.pdf, printed on Sep. 9, 2014.

Product description of "MCP-1 siRNA (h): sc-43913", Santa Cruz Biotechnology, Inc., 1 page, found at www.scbt.com/datasheet-43913-mcp-1-sirna-h.html, printed on Sep. 9, 2014.

Press Release "Turning spiegelmers into drugs", Noxxon Pharma Ag, 2 pages, found at www.noxxon.com/downloads/FactSheet.pdf, (2014).

Seet, B.T. et al., "Viral chemokine-binding proteins", Journal of Leukocyte Biology, vol. 72, pp. 24-34, (2002).

International Search Report dated Mar. 3, 2016 for PCT Application No. PCT/US2015/054758, 20 pages.

Choi, H-R. et al., "Oligosaccharides of hyaluronic acid increased epidermal cell stemness by modulation of integrin expression", Journal of Cosmetic Dermatology, vol. 11, No. 4, pp. 290-296, (2012).

Pascual-Marti, M.C. et al., "Supercritical fluid extraction of resveratrol from grape skin of vitis vinifera and determination by HPLC", Talanta vol. 54, pp. 735-740, (2001).

Khanna, S. et al., "Dermal wound healing properties of redox-active grape seed proanthocyanidins", Free Radical Biology & Medicine, vol. 33, No. 8, pp. 1089-1096, (2002).

\* cited by examiner

METHOD OF REDUCING SCARRING

BACKGROUND

Wound healing is a complex process, and involves the regulation of numerous cellular functions including the interactions of fibroblasts/fibrocytes, osteoblasts, chondrocytes, endothelial cells, inflammatory cells, epithelial cells and smooth muscle cells, with the extracellular matrix. Normal healing results in scar formation in humans. However, it is well known that certain animals, and even the human fetus, are capable of regenerative healing of wounds which is indistinguishable from surrounding skin.

Although the intricate details of wound healing are still being discovered, the process follows along a typical time line having four phases:

Hemostasis Phase—This phase includes vasoconstriction lasting for the first 5-10 minutes after the injury.

Inflammation Phase—This phase includes vasodilation and a cellular response by inflammatory macrophages, neutrophils and fibroblasts. Neutrophils undergo cannbilaization to produce transforming growth factor beta-1 (TGF-$\beta$1), which stimulates production of type I collagen (the mature collagen present in nomal skin) and stimulates fibroblast to myofibroblasts mediated by hyaluronic acid and epidermal growth factor receptor (EGFR). Bacteria, foreign particles and damaged cells are removed from the wound. Vasodilation starts at about 10 minutes after the initial injury, and the cellular response typically starts 30 minutes after the initial injury. Keratinocytes detach from the basement membrane and migrate to cover the exposed wound and connective tissue, and the wound clot is replaced with epithelial cells and granulation tissue (type III collagen). Differentiating keratinocytes also produce TGF-$\beta$1. The cellular response may last 7 to 8 days.

Proliferation Phase—This phase includes re-epithelialization of the wound, fibroplasia, including collagen synthesis and wound contraction. During this phase skin cells multiply and spread, covering the wound. Re-epithelialization typically starts 24 hours after the injury. Fibroplasia typically starts in 3 to 4 days after the injury. Myofibroblasts (present in granulation tissue) express alpha-smooth muscle actin and are responsible for wound contraction, which typically starts 7 days after the injury.

Remodeling Phase—This phase includes scar/collagen remodeling. The newly formed collagen matrix becomes cross linked and organized starting about 3 weeks from wound initiation and lasting as long as 1 year.

Scar formation is a typical response for normal healing in humans. As compared with normal skin, a scar contains an overproduction of type III and type I collagens, and the mixture is disorganized. The scar itself is not very elastic and is of a different color than normal skin. The scar is also missing the layer of kertinocytes found on normal skin. Furthermore, depending on how deep was the original wound, the scar may be missing the normal underlying layers of muscle, fat, blood vessels, and many layers of the skin; these missing layers may result in the scar forming a depression compared to the level of the surrounding skin.

Some animals are capable of scar free healing. In axolotls, there is a substantial reduction in neutrophil infiltration and a relatively long delay in production of new extracellular matrix during scar free healing. Studies with athymic nude mice indicate that up-regulation in metalloproteinase-9 (MMP-9) throughout the remodeling phase may contribute to scar free healing. Matrix metalloproteinases (MMP's) are a family of zinc dependent enzymes capable of degradation of extracellular matrix and are vital to the remodeling of the matrix and migration of cells. During normal human wound healing, MMP-9 degrades the type IV collagen of the basement membrane allowing keratinocytes to detach from the basement membrane and migrate to cover the exposed wound and connective tissue.

Human oral healing of wounds results in little to no scar formation. Oral mucosal wounds show a robust early up-regulation of MMP-1, MMP-2 and MMP-9 at 3 days after the initial injury, as compared to skin wounds at 14 days after the initial injury. The human fetus, which also shows scar free healing, is surrounded by amniotic fluid which contains high molecular weight hyaluronic acid. High molecular weight hyaluronic acid is known to increase expression of MMP-2 and MMP-9. Although high molecular weight hyaluronic acid application at a wound site can reduce scarring, a scar is nevertheless still formed.

Resveratrol (trans-3,4',5-trihydroxystilbene), a stilbenoid, is a grape polyphenol present in various plants, some food products, red wine and grapes. Resveratrol has anti-inflammatory, anti-carcinogenic and anti-oxidant properties, and has been extensively studied. Huge interest in resveratrol was created when it was discovered that it was able to active the SIRT1 gene, a gene implicated in the life span extension associate with calorie-restricted diets. However, resveratrol is poorly absorbed when consumed as a dietary supplement, and is subject to metabolic degradation, and beneficial effect have been difficult to observe in human clinical studies.

SUMMARY

In a first aspect, the present invention is a method for reducing scarring comprises applying into a wound a composition comprising resveratrol. The wound was formed at most one day before the applying, and no part of the skin surface of the wound is more than 3 cm from uninjured skin.

In a second aspect, the present invention is a composition for reducing scarring by applying into a wound which was formed at most one day before the applying, and in which no part of the skin surface of the wound is more than 3 cm from uninjured skin, the composition comprising resveratrol.

In a third aspect, the present invention is a use of resveratrol to prepare a composition for reducing scarring by applying into a wound, wherein the wound was formed at most one day before the applying, and no part of the skin surface of the wound is more than 3 cm from uninjured skin.

DETAILED DESCRIPTION

The present invention makes use of the discovery that compositions containing resveratrol, when applied into a wound soon after the initial injury, will greatly reduce scarring. In some cases, compositions containing resveratrol may even eliminate scarring altogether. Also discovered is that these effects of resveratrol may be enhanced when combined with one or more additional active agents.

It has been discovered that if a wound or incision is completely healed in less than 3 days, before fibroplasia begins, then no scar will be formed at the location of the wound or incision. Therefore composition containing resveratrol will allow for scar free healing when applied to wounds or incisions that do not have any injured or missing tissue which is more than 3 cm from uninjured tissue. Examples include almost all incisions purposefully created by a surgeon, because the surgeon is able to bring the edges of the skin at the location of the incision to well within 3 cm of each other. Preferably, no part of the skin surface of the wound is more than 3 cm from uninjured skin, more preferably no part of the skin surface of the wound is more than 2 cm from uninjured skin, even more preferably no part of the skin surface of the wound is more than 1 cm from uninjured skin, and most preferably no part of the skin surface of the wound is more than 0.5 cm from uninjured skin.

Compositions containing resveratrol, either as the sole active agent or in combination with other active agents, is preferably applied to a wound or incision at any time from prior to formation of a wound or incision up until at most one day after the formation of a wound or incision; more preferably prior to formation of a wound or incision, up until at most 1 hour after the formation of a wound or incision; and most preferably prior to formation of a wound or incision, up until at most 10 minutes after the formation of a wound or incision. Preferably, only a single application of a composition containing resveratrol is used. For example, a composition containing resveratrol may be applied topically to an incision site, or injected below an incision site, then the skin may be cut, optionally followed by closing the incision; for example the deep structures which have been cut under the skin may be tied down using VICRYL™ (polyglactin 910) sutures, and then skin sutured or sealed using DERMA-BOND ADVANCED™ topical skin adhesive or NEW-SKIN® liquid bandage. Alternatively, a composition containing resveratrol may be applied to the incision or wound after it is formed, followed by closing the wound or incision as described above.

Preferably, resveratrol is present in a composition at a concentration of at least 0.01 micromoles/liter, more preferably at a concentration of at least 0.10 micromoles/liter, and most preferably at a concentration of at least 0.50 micromoles/liter. Preferably, resveratrol is present in the composition at a concentration of at most 100 micromoles/liter, more preferably at most 40 micromoles/liter. Examples include 0.75, 0.80, 0.90, 1.0, 1.25, 1.5, 1.6, 1.7, 1.8, 1.9, 2.0, 2.1, 2.19, 2.2, 2.3, 2.4, 2.5, 2.6, 2.7, 2.8, 2.9, 3.0, 3.25, 3.5, 3.75, 4.0, 4.25, 4.5, 4.75, 5.0, 5.5, 6.0, 6.5, 7.0, 7.5, 8.0, 9.0, 10.0, 15.0, 20.0, 25.0, 30.0 and 35.0 micromoles/liter. Concentrations of resveratrol above 100 micromoles/liter appear to be cytotoxic to keratinocytes.

In some forms, such as gels and pastes, the delivery medium limits contact with the surrounding tissue, the surrounding tissue rapidly degrades the resveratrol, and the tissue itself will absorb the resveratrol, resulting in a much lower effective concentration of resveratrol. In those cases, the concentration of resveratrol may optionally be increased 10 fold. In those cases, preferably resveratrol is present in a composition at a concentration of at least 0.1 micromoles/liter, more preferably at a concentration of at least 1.0 micromoles/liter, and most preferably at a concentration of at least 5.0 micromoles/liter. Preferably, resveratrol is present in those compositions at a concentration of at most 1000 micromoles/liter, more preferably at most 400 micromoles/liter. Examples include 7.5, 8.0, 9.0, 10, 12.5, 15, 16, 17, 18, 19, 20, 21, 21.9, 22, 23, 24, 25, 26, 27, 28, 29, 30, 32.5, 35, 37.5, 40, 42.5, 45, 47.5, 50, 55, 60, 65, 70, 75, 80, 90, 100, 150, 200, 250, 300 and 350 micromoles/liter.

Resveratrol has a very low solubility in water, however only that portion which is dissolved in water will exert its effects. Furthermore, if the resveratrol is applied dissolved in a hydrophobic medium, it may slowly diffuse into the surrounding aqueous medium, and undesirably extend the effective application time. Therefore, it is preferable that the resveratrol be applied as a solution in an aqueous medium. For ease of application in a clinical setting, preferably the aqueous medium is a gel, paste, foam, suspension or thickened solution. Examples include aqueous compositions containing hydroxypropyl methylcellulose, high molecular weight hyaluronic acid, polyethylene glycol, agar, dextrin, pectin, trehalose, xanthan gum, polyoxyethylene alkyl ethers, chitosan, guar gum and sodium alginate. Other vehicles, adjuvants and excipients, which are hydrophilic or have hydrophilic moieties, and are compatible which application into wounds, may also be used. Other pharmaceutically acceptable adjuvant, excipients and vehicles may also be included.

Premeasured amounts of the compositions containing resveratrol may also be used. These are referred to as unit dosage forms, since each premeasured amount is intended to be used on a single patient for one or more application, all used at the same time. Examples include prefilled syringes, pouches, packets and tubes. Another example would be a tube or dispenser which may be used to form foam of its contents just prior to application, for example by shaking or using a foaming agent. A self-foaming tablet, which forms foam when placed into water, could also be used. The volume of material present in these unit dosage forms may be at least 0.1 to 100 ml, or 1 to 50 ml. including 2, 3, 4, 5, 6, 7, 8, 9, 10, 11, 12, 13, 14, 15, 20, 25, 30, 35, 40 and 45 ml.

Other active agents may be included, such as other activators of SIRT1; HDAC2 (a class I histone deacetylase) inhibitors, such as trichostatin A; agents which stimulate the production of certain growth factors such as EGF, FGF-10 and IGF-1; luteolin; tretinoin (all-trans retinoic acid); and high molecular weight hyaluronic acid.

Although it is not known exactly how resveratrol reduces scarring, resveratrol does up-regulate and increase the expression of a variety of agents which are involved in wound healing. One possible explanation is that resveratrol causes the over-expression of MMP-9, interleukin-8 (IL-8) and SIRT1, and increases expression of EGFR on the keratinocyte membrane and nucleus. SIRT1 may then promote differentiation, motility and proliferation of keratinocytes, and deacetylation and inactivation of p53 protein thus inhibiting p53-dependent cell death from apoptosis in response to stress in human tenocytes (fibroblast-like tendon cells). SIRT1 may induce nitric oxide (NO) production, which inhibits class I HDAC 2 from blocking growth factors, including epithelial growth factor, keratinocyte growth factor 2, fibroblast growth factor 10 (FGF-10), and insulin-like growth factor 1 (IGF-1). SIRT1 may also decrease inflammation and apoptosis through a variety of mechanisms. IL-8 has a direct and profound stimulatory effect on the migration of keratinocytes, which is likely due via the PLC-gamma pathway, and furthermore IL-8 may recruit neutrophils. As noted above, MMP-9 degrades the type IV collagen of the basement membrane. EGFR may cause keratinocyte and fibroblast migration and may protect and repair tissue through nuclear DNA repair. Resveratrol may also inhibit NF-kB dependent proinflammatory and matrix degrading gene products induced by IL-1β and nicotinamide.

EXAMPLES

Example 1: In Vivo Application of Various Compositions Containing Resveratrol in a Rat Model In this example, 15 Sprague Dawley Rats, 6-8 weeks old, will be placed randomly into 5 different groups, Study Groups 1-5, resulting in 3 animals per study group. An incision, 2 cm in length, will be made on both the right and left shoulder of each rat: the left side will be an untreated control, while the right side will be treated with the Compositions 1-5, with the Study Group number corresponding to the Composition number.

The Compositions 1-5 are: (1) 0.5 g resveratrol in 1.0 cc aqueous hydroxypropyl methyl cellulose gel (resveratrol concentration=2.19 micromoles/liter); (2) 0.5 g resveratrol in 1.0 cc aqueous high molecular weight hyaluronic acid gel (resveratrol concentration=2.19 micromoles/liter); (3) 0.5 g resveratrol and 0.5 g tretinoin in 1.0 cc aqueous hydroxypropyl methyl cellulose gel (resveratrol concentration=2.19 micromoles/liter); (4) 0.5 g resveratrol and 0.5 g luteolin in 1.0 cc aqueous hydroxypropyl methyl cellulose gel (resveratrol concentration=2.19 micromoles/liter); and (5) resveratrol powder.

After each incision is made, the resveratrol containing composition will be applied to the right incision just prior to closure using interrupted 5-0 nylon sutures. The left incision will also be closed using interrupted 5-0 nylon sutures. Each incision will be photographed and measurements will be taken, each day for 7 days. On the 4$^{th}$ day, serum blood samples will be taken for systemic absorption assay. On the 7$^{th}$ day, a punch biopsy will be taken from each test and control incision.

Since each skin flap of the incisions is very close together, when the composition containing resveratrol is applied soon after the incision is made, the incision on the right shoulder heals before fibroplasia begins, so no scar is formed. This is in contrast to the otherwise identical incision on the left side, where no resveratrol is applied, which displays a typical scar.

REFERENCES

Ehrlich H, Krummel T: Regulation of wound healing from a connective tissue perspective. *Wound Repair & Regeneration* 1996, 4(2):203-210.

Leung A, Crombleholme T M, Keswani S G: Fetal wound healing: implictions for minimal scar formation. *Curr Opin Pediatr* 2012, June 24(3): 371-8.

Manuel J, Gawronska-Kozak B: Matrix metalloproteinase 9 (MMP-9) is upregulated during scarless wound healing in athymic nude mice. *Matrix Biology* 2006, 25:505-514.

Seifert A W, Monaghan J, Voss S, Maden M: Skin regernation in adult axolotls: a blueprint for scar-free healing in vertebrates. *PLoS One* 2012, 7: 4

Polette M, Nawrocki-Raby B, Gilles C, Clavell C, Birembaut P: Tumor invasion and matrix metalloproteinases. *Crit. Rev. Oncol Hematol* 2004, 49:179-186.

Salo T, Makela M, Kylmaniemi M, Autio-Harmainen H, Larjava H: Expression of matrix metalloproteinase-2 and -9 during early human wound healing. *Lab Invest* 1994, February; 70(2):176-82.

Giannelis, G: Matrix metalloproteinases in scarless wound healing. *Electronic Theses and Dissertations* 2008 to 2011, July. (Available at hdl.handle.net/2429/36241).

Guo M S, Wu Y Y, Liang Z B: Hyaluronic acid increases MMP-2 and MMP-9 expressions in cultured trabecular meshwork cells from patients with primary open-angle glaucoma. *Mol Vis* 2012, 18:11175-81.

Ndiaye M, Philippe C, Mukhtar H, Ahmad N: The grape antioxidant resveratrol for skin disorders: promise, prospects, and challenges. *Arch Biochem Biophys* 2011, April 15:508(2): 164-70.

Gweon E, Kim S: Resveratrol induces MMP-9 and cell migration via the p38 kinase and PI-3K pathways in HT1080 human fibrosarcoma cells. *Oncol Rep* 2013, Feb. 29(2): 826-34.

Ghosh S, Liu B, Zhou Z: Resveratrol activates SIRT1 in a Lamin A-dependent manner. *Cell Cycle* 2013 Mar. 15; 12(6):872-6.

Blander G, Bhimavarapu A, Mammone T, Maes D, Elliston K, Reich C, Matsui M S, Buarente L, Loureiro J J. SIRT1 promotes differentiation of normal human keratinocytes. *J Invest Dermatol* 2009 January; 129(1):41-9.

Thompson N L, Flander K C, Smith J M, Ellingsworth L R, Roberts A B, Sporn M B. Expressions of transforming growth factor-beta 1 in specific cells and tissues of adult and neonatal mice. *J Cell Biol*. 1989:108:661-9.

Midgley A, Rogers M, Hallett M, Clayton A, Bowen T, Phillips A, Steadman R. Transforming growth factor-beta 1 (TGF-B1)-stimulated fibroblast to myofibroblast differentiation is mediated by hyaluronan (HA)-facilitated epidermal growth factor receptor (EGFR) and CD44 colocalisation in lipid rafts. *J Biol Chem* 2013 Apr. 15 [Epub ahead of print].

Busch F, Mobashieri A, Shayan P, Stahlmann R, Shakibaei M. Sirt-1 Is Required for the Inhibition of Apoptosis and Inflammatory Responses in Human Tenocytes. *J Biol Chem* 2012 Jul. 27; 287(31):25770-25781.

Spallotta F, Cencioni C, Straino S, Nanni S, Rosati J, Artuso S, Manni I Colussi C, Piaggio G, Martelli F, Valent S, Mai A, Caposgrassi M D, Faretti A, Gaetano C. A Nitric Oxide-dependent Cross-talk between Clas I and II Histone Deacetylases Accelerates Skin Repari. *J Bio Chem.* 2013 Apr. 19; 288(16):11004-12.

Pastore S, Lulli D, Maurelli R, Dellambra E, DeLuca C, Korkina L G; Resveratrol induces long-lasting IL-8 expression and peculiar EGFR activation/distributio in human keratinocytes:mechanisms and implications for skin administration. *PLoS One* 2013:8(3):e59632.

Jiang W G, Sanders A J, Ruge F, Harding K G. Influence of interleukin-8 (IL-8) and IL-8 receptors on the migration of human keratinocytes, the role of PLC-gamma and potential clinical implications. *Exp The Med* 2012 February; 3(2):231-236.

Steiger S, Harper J L. Neutrophil cannibalism triggers transforming growth factor beta1 production and self regulation of neutrophil inflammatory function in monosodium urate monohydrate crystal-induced inflammation in mice. *Arthritis Rheum* 2013 March: 65(3):815-23.

Holian O, Walter R J. Resveratrol inhibits the proliferation of normal human keratinocytes in vitro. *J Cell Biochem Suppl* 2001; Suppl 36:55-62.

Kim J J, Kim S J, Kim S Y, Park S H, Kim E C. The role of SIRT1 on angiogenic and odontogenic potential in human dental pulp cells. *J Endod* 2012 July; 38(7):899-906.

Williams L D, et al.; Safety studies conducted on high-purity trans-resveratrol in experimental animals. *Food Chem Toxicol,* 2009 September; 47(9):2170-82.

Polonini H C, et al. Photoprotective activity of resveratrol analogues. *Bioorg Med Chem,* 2013 Feb. 15; 21(4):964-8.

Hung C F, Lin Y K, Huang Z R, Fang J Y. Delivery of resveratrol, a red wine polyphenol, from solutions and hydrogels via the skin. *Biol Pharm Bull.* 2008 May; 31(5):955-62.

Alonso C, Marti M, Martinez V, Rubio L, Parra J L, Coderch L. Antioxidant cosmeto-textiles: skin assessment. *Eur J Pharm Biopharm.* 2013 May; 84(1):192-9. doi: 10.1016/j.ejpb.2012.12.004. Epub 2012 Dec. 20.

Machesney M, Tidman N, Waseem A, Kirby L, Leigh I. Activated keratinocytes in the epidermis of hypertrophic scars. *Am J Pathol.* 1998 May; 152(5):1133-41.

Fagone E, Conte E, Gili E, Fruciano M, Pistorio M P, Lo Furno D, Giuffrida R, Crimi N, Vancheri C. Resveratrol inhibits transforming growth factor-β-induced proliferation and differentiation of ex vivo human lung fibroblasts into myofibroblasts through ERK/Akt inhibition and PTEN restoration. *Exp Lung Res.* 2011 April; 37(3):162-74. doi: 10.3109/01902148.2010.524722. Epub 2011 Jan. 26.

Sheu S Y, Chen W S, Sun J S, Lin F H, Wu T. Biological characterization of oxidized hyaluronic acid/resveratrol hydrogel for cartilage tissue engineering. *J Biomed Mater Res A.* 2013 Apr. 18. doi: 10.1002/jbm.a.34653. [Epub ahead of print]

Fearmonti R, Bond J, Erdmann D, Levinson H. A review of scar scales and scar measuring devices. *Eplasty.* 2010 Jun. 21; 10:e43.

Busch F, Mobasheri A, Shayan P, Stahlmann R, Shakibaei M. Sirt-1 is required for the inhibition of apoptosis and inflammatory responses in human tenocytes. J Biol Chem. 2012 Jul. 27; 287(31):25770-81. doi: 10.1074/jbc.M112.355420. Epub 2012 Jun. 11.

Nayor D, Kiefer D. Living longer, Healthier Lives with Resveratrol. *Le Magazine* 2008 February (available at www.lef.org).

Resveratrol. en.wikipedia.org/wiki/Resveratrol (downloaded Jun. 21, 2013).

Amato et al. U.S. Pat. Pub., Publication no. US 2011/0245345 (Oct. 6, 2011).

McKay et al. U.S. Pat. Pub., Publication no. US 2011/0038965 (Feb. 17, 2011).

NEW-SKIN® Cover. Protect. Prevent. newskinproducts.com/products.aspx (downloaded Jun. 20, 2013).

What is claimed is:

1. A method for reducing scarring, comprising: applying into a wound, a composition comprising resveratrol,
    wherein the wound was formed at most one day before the applying,
    no part of the skin surface of the wound is more than 3 cm from uninjured skin, and
    the composition comprising resveratrol is applied once into the wound.

2. The method of claim 1, wherein an amount of resveratrol present in the composition is 10 to 1000 micromoles/liter.

3. The method of claim 1, wherein the wound was formed at most one hour before the applying.

4. The method of claim 1, wherein no part of the skin surface of the wound is more than 0.5 cm from uninjured skin.

5. The method of claim 1, wherein the composition is a gel, paste, foam, suspension or thickened solution.

6. The method of claim 1, wherein the composition is a gel or thickened solution.

7. The method of claim 1, wherein the composition further comprises at least one member selected from the group consisting of hydroxypropyl methylcellulose, high molecular weight hyaluronic acid, polyethylene glycol, agar, dextrin, pectin, trehalose, xanthan gum, polyoxyethylene alkyl ethers, chitosan, guar gum and sodium alginate.

8. The method of claim 1, wherein the composition further comprises at least one member selected from the group consisting of a SIRT1 activator; a HDAC2 inhibitor: an agent which stimulates the production of EGF, FGF-10 or IGF-1; luteolin; tretinoin; and high molecular weight hyaluronic acid.

9. The method of claim 1, wherein the wound is an incision.

10. The method of claim 1, wherein an amount of resveratrol present in the composition is 10 to 1000 micromoles/liter,
    the composition further comprises hydroxypropyl methylcellulose or high molecular weight hyaluronic acid,
    the composition is a gel, paste, foam, suspension or thickened solution, and
    the wound is an incision.

11. The method of claim 1, wherein the applying comprises injecting the composition comprising resveratrol into the wound.

* * * * *